US012735489B2

(12) United States Patent
Wang et al.

(10) Patent No.: US 12,735,489 B2
(45) Date of Patent: Sep. 15, 2026

(54) USE OF FCGAMMARIII INHIBITOR IN PREPARATION OF MEDICAMENT FOR TREATING PULMONARY FIBROSIS

(71) Applicant: Institute of Basic Medical Sciences of Chinese Academy of Medical Sciences, Beijing (CN)

(72) Inventors: Jing Wang, Beijing (CN); Tiantian Zhang, Beijing (CN); Xianmei Qi, Beijing (CN); Xiaona Li, Beijing (CN)

(73) Assignee: Institute of Basic Medical Sciences of Chinese Academy of Medical Sciences, Beijing (CN)

( * ) Notice: Subject to any disclaimer, the term of this patent is extended or adjusted under 35 U.S.C. 154(b) by 1014 days.

(21) Appl. No.: 17/937,529

(22) Filed: Oct. 3, 2022

(65) Prior Publication Data

US 2023/0406938 A1 Dec. 21, 2023

(30) Foreign Application Priority Data

Jun. 20, 2022 (CN) ......................... 202210696605.3

(51) Int. Cl.

| | |
|---|---|
| ***A61P 11/00*** | (2006.01) |
| ***C07K 16/28*** | (2006.01) |
| ***C12N 15/113*** | (2010.01) |

(52) U.S. Cl.

CPC ............ *C07K 16/283* (2013.01); *A61P 11/00* (2018.01); *C12N 15/1138* (2013.01); *C12N 2310/14* (2013.01); *C12N 2310/141* (2013.01); *C12N 2310/531* (2013.01)

(58) Field of Classification Search

CPC ........ C07K 16/283; A61P 11/00; A61P 29/00; C12N 15/1138; C12N 2310/14; C12N 2310/141; C12N 2310/531; A61K 2039/505; A61K 45/00

See application file for complete search history.

*Primary Examiner* — Stacey N Macfarlane

(74) *Attorney, Agent, or Firm* — DLA Piper LLP (US)

(57) ABSTRACT

The present disclosure provides use of an FcγRIII inhibitor for treating pulmonary fibrosis, and belongs to the technical field of biomedicine. Results indicate that FcγRIII mediates macrophage phagocytosis of silica particles, FcγRIII knock-out can effectively relieve pulmonary inflammatory response and fibrotic lesions in mice with silicosis, and further intratracheal administration of an anti-FcγRIII antibody significantly delays disease progression of mice at fibrosis phase. Therefore, the present disclosure first sets forth that the FcγRIII inhibitors can be used for treating pulmonary fibrosis, which is of importance to the screening of new drugs and provides a new idea for treatment of pulmonary fibrosis.

1 Claim, 9 Drawing Sheets

Specification includes a Sequence Listing.

SEQUENCE LISTING

```
Sequence total quantity: 7
SEQ ID NO: 1            moltype = DNA  length = 18
FEATURE                 Location/Qualifiers
source                  1..18
                        mol_type = other DNA
                        note = Primer Actin-F
                        organism = synthetic construct
SEQUENCE: 1
ggagggggtt gaggtgtt                                               18
```

-continued

```
SEQ ID NO: 2            moltype = DNA  length = 23
FEATURE                 Location/Qualifiers
source                  1..23
                        mol_type = other DNA
                        note = Primer Actin-R
                        organism = synthetic construct
SEQUENCE: 2
gtgtgcactt ttattggtct caa                                          23

SEQ ID NO: 3            moltype = DNA  length = 18
FEATURE                 Location/Qualifiers
source                  1..18
                        mol_type = other DNA
                        note = Primer FcgammaRIII-F
                        organism = synthetic construct
SEQUENCE: 3
agacaggcag agtgcagc                                                18

SEQ ID NO: 4            moltype = DNA  length = 20
FEATURE                 Location/Qualifiers
source                  1..20
                        mol_type = other DNA
                        note = Primer FcgammaRIII-R
                        organism = synthetic construct
SEQUENCE: 4
gtcccttcgc acatcagtgt                                              20

SEQ ID NO: 5            moltype = DNA  length = 58
FEATURE                 Location/Qualifiers
source                  1..58
                        mol_type = other DNA
                        note = Primer shRNA-F
                        organism = synthetic construct
SEQUENCE: 5
ccgggctaag ggttgatggc atagcctcga ggctatgcca tcaaccctta gctttttg    58

SEQ ID NO: 6            moltype = DNA  length = 58
FEATURE                 Location/Qualifiers
source                  1..58
                        mol_type = other DNA
                        note = Primer shRNA-R
                        organism = synthetic construct
SEQUENCE: 6
aattcaaaaa gctaagggtt gatggcatag cctcgaggct atgccatcaa cccttagc    58

SEQ ID NO: 7            moltype = DNA  length = 21
FEATURE                 Location/Qualifiers
source                  1..21
                        mol_type = other DNA
                        note = shRNA-3 1258-1278 functional sequence
                        organism = synthetic construct
SEQUENCE: 7
gctaagggtt gatggcatag c                                            21
```

USE OF FCGAMMARIII INHIBITOR IN PREPARATION OF MEDICAMENT FOR TREATING PULMONARY FIBROSIS

CROSS REFERENCE TO RELATED APPLICATION

This patent application claims the benefit and priority of Chinese Patent Application No. 202210696605.3, filed on Jun. 20, 2022, the disclosure of which is incorporated by reference herein in its entirety as part of the present application.

REFERENCE TO AN ELECTRONIC SEQUENCE LISTING

The contents of the electronic sequence listing (sequencelisting.xml; Size: 107,643 bytes; and Date of Creation: Feb. 28, 2021) is herein incorporated by reference in its entirety.

TECHNICAL FIELD

The present disclosure belongs to the technical field of biomedicine, and particularly relates to use of an FcγRIII inhibitor in for treating pulmonary fibrosis.

BACKGROUND ART

Pulmonary fibrosis is a chronic progressive interstitial disease caused by multiple factors, which clinically manifests as impairment of pulmonary function and leads to lung failure at the end stage of the disease. Pulmonary fibrosis is divided into idiopathic pulmonary fibrosis of unknown etiology and pulmonary fibrosis secondary to other etiological factors. Silicosis is one of pulmonary fibrotic diseases, which is caused by long-term inhalation of crystalline silica and is one of major occupational diseases. Because the disease is difficult to reverse, it is a serious danger to the health of professionals. At present, clinical treatment is mainly used to improve symptoms and related complications of patients. Comprehensive treatment improves cough, chest pain, and short of breath, and controls pulmonary infection and pulmonary tuberculosis. Bronchoalveolar lavage is one of clinically available means, which help clear dust and secretions deposited in the airway, but it has not been observed that it helps delay the disease progression. Lung transplantation is a treatment measure taken at the end stage of the disease and is the most promising therapy to prolong the survival time of patients. However, due to the shortness of donor and high surgical difficulty, there is a small population benefiting therefrom. Therefore, seeking for an effective drug capable of alleviating the progression of silicosis and reducing the mortality of late silicosis admits of no delay.

Crystalline silica is difficult to be removed from the body due to physicochemical properties thereof, and stimulating long-term chronic inflammatory responses in the body is one of the key etiologies of silicosis and fibrosis. At the early stage, the present laboratory found from transcriptome analysis that phagosomal/lysosomal pathway changed significantly in lung tissues of silicotic patients. According to plenty of evidence, silica is phagocytized by macrophages and finally reaches lysosomes; its surface properties, silica induces a large amount of reactive oxygen species (ROS) production, leading to the swelling and rupture of lysosomes, and thus resulting in secretion of inflammatory factors from macrophages and even apoptosis. If the apoptotic macrophages cannot be cleared in time, it will cause them to undergo post-apoptotic necrosis leading to further inflammatory responses; released silica are phagocytized by new macrophages, and the whole course moves in circles. Therefore, blocking macrophage phagocytosis may be one of the ways to block this cycle, and it has been reported that blocking of phagocytosis-related receptors plays a protective role in silicosis. The class A scavenger receptors of alveolar macrophages are now well accepted, particularly macrophage receptor with collagenous structure (MARCO). MARCO can directly mediate the phagocytosis of silica, but blocking MARCO does not fully block subsequent inflammatory and fibrotic responses, suggesting that MARCO may not be the only receptor that plays a role in the phagocytosis of silica.

Receptors for Fc fragment of immunoglobulin G (Fc γ R) on cell surface participates in cell phagocytosis. In mice, the acceptor family is mainly divided into four categories: FcγRI, FγRIIb, FcγRIII, and FcγRIV. Among them, FcγRIII is an agonistic low-affinity receptor, which is widely expressed in phagocytes and participates in the development and progression of multiple diseases related to the abnormal inflammatory immune response. However, whether low-affinity receptor FcγRIII participates in the development and progression of silicosis has not been reported yet.

SUMMARY

In view of this, an objective of the present disclosure is to provide a method for treating pulmonary fibrosis comprising administering a composition comprising an FcγRIII inhibitor.

To achieve the above objective, the present disclosure provides the following technical solutions:

Methods of treating pulmonary fibrosis comprising administering a composition comprising an FcγRIII inhibitor.

Preferably, the composition comprising an FcγRIII inhibitor may include one or more of a regulator for downregulating expression of FcγRIII, a protease for degrading FcγRIII products, a nuclease, and a regulator for reducing the FcγRIII products.

Preferably, the regulator for downregulating expression of FcγRIII may include a reagent for knocking out or silencing FcγRIII.

Preferably, the regulator for reducing the FcγRIII products may include an anti-FcγRIII antibody.

Preferably, the reagent for knocking out or silencing FcγRIII may include an siRNA plasmid, an shRNA plasmid, or an miRNA plasmid.

Preferably, a functional sequence for knockdown in the shRNA plasmid is shown in SEQ ID NO: 7.

Preferably, the composition comprising an FcγRIII inhibitor may inhibit macrophage phagocytosis of silica.

Preferably, the composition comprising an FcγRIII inhibitor may improve pulmonary dysfunction, pulmonary inflammation, and pulmonary fibrosis.

Preferably, the pulmonary fibrosis may include silicosis.

The present disclosure further provides a composition for treating pulmonary fibrosis, including an active ingredient and pharmaceutically acceptable carriers, where the active ingredient is an anti-FcγRIII antibody or an shRNA plasmid.

Compared with the prior art, the present disclosure has the following beneficial effects:

The present disclosure provides for methods of treating pulmonary fibrosis comprising administering a composition comprising an FcγRIII inhibitor. Results indicate that FcγRIII mediates macrophage phagocytosis of silica particles, FcγRIII knockout can effectively relieve pulmonary inflammatory response and fibrotic lesions in mice with silicosis, and further intratracheal administration of an anti-FcγRIII antibody significantly delays disease progression of mice at fibrosis phase. Therefore, the present disclosure first sets forth that the FcγRIII inhibitor is used for treating pulmonary fibrosis, which is of importance to the screening of new drugs and provides a new idea for treatment of pulmonary fibrosis.

BRIEF DESCRIPTION OF THE DRAWINGS

FIG. 2A represents relative mRNA levels of Fcgr3 in lung tissues of mice in the PBS group and the silica group; FIG. 2B is an electrophoretogram of protein expression of FcγRIII in lung tissues of mice in the PBS group and the silica group; and represents protein expression levels of FcγRIII in lung tissues of mice in the PBS group and the silica group;

DETAILED DESCRIPTION OF THE EMBODIMENTS

Figure 1:
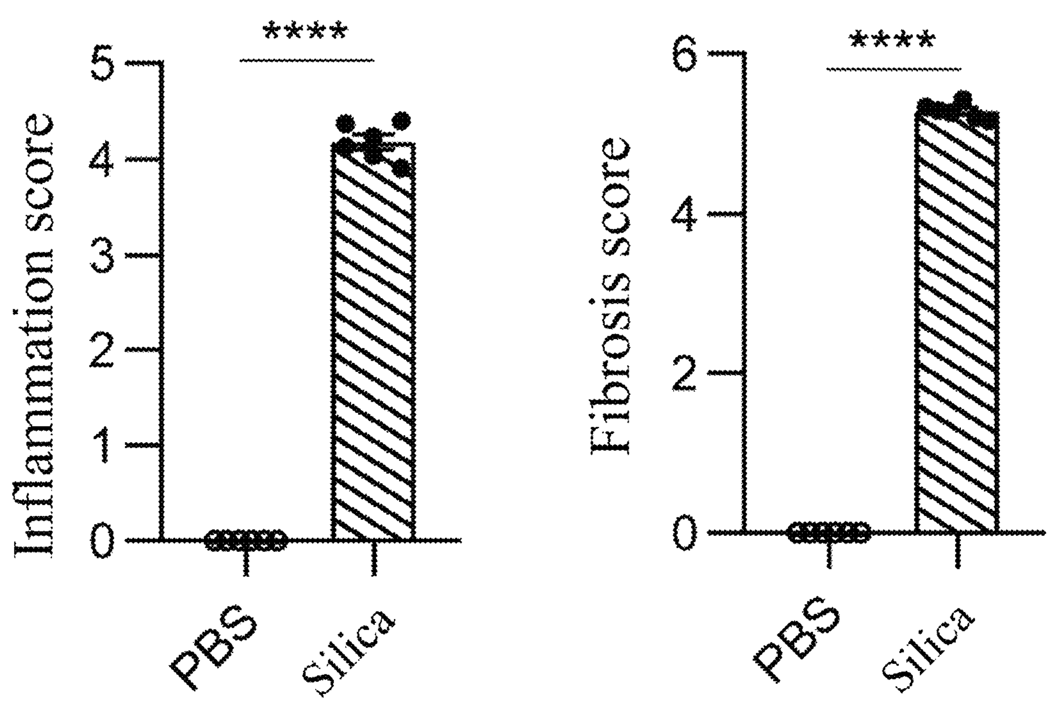
FIG. 1 illustrates inflammation and fibrosis scores of lung tissues of mice in the PBS group and the silica group.

The present disclosure investigates pulmonary fibrosis and discovers a new target FcγRIII for treating pulmonary fibrosis. Therefore, a method of treating pulmonary fibrosis comprising administering a composition comprising an FcγRIII inhibitor is provided.

In the present disclosure, the FcγRIII inhibitor may preferably include one or more of a regulator for downregulating expression of FcγRIII, a protease for degrading FcγRIII products, a nuclease, and a regulator for reducing the FcγRIII products. Further preferably, the regulator for downregulating expression of FcγRIII may include a reagent for knocking out or silencing FcγRIII; furthermore, preferably, the reagent for knocking out or silencing FcγRIII may include an siRNA plasmid, an shRNA plasmid, or an miRNA plasmid. In the present disclosure, siRNA refers to short double-stranded RNA, which is capable of inducing RNA interference by cleaving some mRNAs; the siRNA includes a sense RNA strand having a sequence homologous to mRNA of a target gene and an anti-sense RNA strand complementary thereto; the siRNA may inhibit the expression of the target gene and be used for gene knockdown and gene therapy. In the present disclosure, shRNA (short hairpin RNA) is a single-stranded RNA, which includes a stem part and a loop part formed by hydrogen bonding, is processed and converted into the siRNA by proteins such as Dicer, and implements the same function as the siRNA. In the present disclosure, miRNA refers to 21-23 non-coding RNAs, which regulates gene expression by promoting the degradation of target RNA or inhibiting translation thereof after transcription. In the present disclosure, a functional sequence for knockdown in the shRNA plasmid is GCTAAGGGTTGATGGCATAGC, as shown in SEQ ID NO: 7.

The present disclosure further provides a composition comprising an FcγRIII inhibitor for treating pulmonary fibrosis, including an active ingredient and pharmaceutically acceptable carriers. The active ingredient of the composition comprising an FcγRIII inhibitor is the foregoing FcγRIII inhibitor, for example, the shRNA plasmid or the anti-FcγRIII antibody. The composition comprising an FcγRIII inhibitor further includes pharmaceutically acceptable carriers, and the carriers include a buffer, a vehicle, a stabilizer, or a preservative, for example, starch, lactose, magnesium stearate, sodium sulfite, and ascorbic acid. Routes of administration of the composition comprising an FcγRIII inhibitor provided by the present disclosure may include oral, intravenous, parenteral, intramuscular, subcutaneous, intraperitoneal, intranasal, rectal, or topical administration. In the present disclosure, a dosage of the comprising an FcγRIII inhibitor provided by the present disclosure may be determined by disease type, disease severity, route of administration, age, gender and health conditions of patients. For example, the dosage of the composition comprising an FcγRIII inhibitor provided by the present disclosure may be 0.01 μg to 1,000 mg per day per patient.

In the present disclosure, the composition comprising an FcγRIII inhibitor may inhibit macrophage phagocytosis of silica, and improve pulmonary dysfunction, pulmonary inflammation, and pulmonary fibrosis.

In the present disclosure, pulmonary fibrosis treated by the composition comprising an FcγRIII inhibitor provided by the present disclosure may include silicosis.

The technical solutions provided by the present disclosure will be described in detail below with reference to examples, but they should not be construed as limiting the protection scope of the present disclosure.

In the following examples, the Fcgr3 refers to a gene encoding FcγRIII.

Example 1

A Study of mRNA and Protein Levels of FcγRIII in Lung Tissues of Mice With Silicosis.

1.1 Collection of Lung Tissues of Silica-Induced Fibrotic Mice

Male SPF-grade C57BL/6J mice (Vital River) weighing 25-30 g and aged 8-10 weeks were selected and divided into a control group and a silica group. Each group contained 6 mice. A silicosis mouse model was established by single-dose endotracheal instillation of 40 μL of silica suspension (200 mg/mL), and the control group was given control PBS at an equivalent dose. At 6 weeks after modeling, the mice were sacrificed, lung tissues were quick-frozen in liquid nitrogen and cryopreserved in a −80° C. refrigerator, and repeated freeze-thaw was avoided.

1.2 Hematoxylin-Eosin (HE) Staining of Lung Tissues

A mouse left lung tissue was soaked in a 4% formalin solution for 48 h, dehydrated and embedded as a paraffin block. The paraffin block was stored in a −20° C. refrigerator. The lung tissue was sectioned to a thickness of 5 μm with a microtome, applied on a glass slide, and dried in a 60° C. oven. The sections were deparaffinized into water in xylene and gradient alcohol successively, dip-dyed in a hematoxylin staining solution for 11 min, rinsed with tap water, subjected to color separation with hydrochloric acid-alcohol, rinsed with tap water for 5 min, dip-dyed in an eosin staining solution for 9 min, and followed by conventional dehydration, permeabilization, and mounting; finally, the slides were photographed under a bright-field microscope, and photos were scored. The inflammation scoring criteria are shown in Table 1.

TABLE 1

The inflammation scoring criteria

| Inflammation grade | Typical manifestations corresponding to inflammation grade |
|---|---|
| 0 | No inflammation or fibrosis |
| 1 | Mild inflammation changes and partial alveolar enlargement, but no fibrotic nodule |
| 2 | Mild to moderate inflammation changes, without structural lung damage |
| 3 | Moderate inflammation changes with alveolar septal thickening |
| 4 | Moderate to severe inflammation changes with pneumonia, fibrosis, and alveolar septal destruction |
| 5 | Severe inflammation changes with obvious parenchymal destruction |

1.3 Masson Staining of Lung Tissues

The above lung tissue sections were preheated in the oven and deparaffinized into water according to the above method. The hematoxylin staining solution, fushsin staining solution, phosphomolybdic acid, and aniline blue were successively added dropwise on the sections for staining according to the instructions. Notably, color separation in hydrochloric acid-alcohol was needed and bluing was performed in tap water after hematoxylin staining; color separation in 1% acetic acid was needed after aniline blue staining. Subsequently, the sections were dehydrated in three vats of 100% ethanol successively, permeabilized in two vats of xylene, and finally mounted with neutral resin; the slides were photographed under a microscope and scored. The pulmonary fibrosis scoring criteria are shown in Table 2.

TABLE 2

The pulmonary fibrosis scoring criteria

| Fibrosis grade | Typical manifestations of different grades of fibrosis |
|---|---|
| 0 | Alveolar septum: no fibrosis<br>Lung structure: normal lungs |
| 1 | Alveolar septum: independent mild fibrotic changes (alveolar septum ≤3-fold normal thickness)<br>Lung structure: partial alveolar space enlargement, and decreased alveolar space, but no fibrotic nodule |
| 2 | Alveolar septum: obvious fibrotic changing (septum >3-fold normal thickness), with nodular formation<br>Lung structure: partial alveolar space enlargement, and decreased alveolar space, but no fibrotic nodule |
| 3 | Alveolar septum: continuous fibrosis in full view (septum >3-fold normal thickness)<br>Lung structure: partial alveolar space enlargement, and decreased alveolar space, but no fibrotic nodule |
| 4 | Alveolar septum: variable<br>Lung structure: a single fibrotic nodule (accounting for 10% of the field of view) |
| 5 | Alveolar septum: variable<br>Lung structure: a fused fibrotic nodule (accounting for >10% but ≤50% of the field of view), but the lung structure being still present |
| 6 | Alveolar septum: variable, but mostly absent<br>Lung structure: a large continuous fibrotic nodule (accounting for >50% of the field of view), but most of the lung structure vanishing |
| 7 | Alveolar septum: absent<br>Lung structure: alveoli almost being covered with fibrotic nodules,<br>but with five spaces |
| 8 | Alveolar septum: absent<br>Lung structure: the field of view being completely covered with fibrotic nodules |

Results in FIG. 1 indicate that silica-treated mice had obvious pulmonary inflammation and fibrosis compared with the control group, suggesting that the modeling was successful.

1.4 qPCR Assay

To investigate the expression of FcγRIII, the inventors detected mRNA levels of FcγRIII in lung tissues of mice with silicosis. Separately, 50 mg each of the above cryopreserved lung tissues were weighed, RNA was extracted from the above mouse lung tissues by the TRIZOL method, and the RNA was reverse transcribed into cDNA using a reverse transcription kit; subsequently, real-time PCR assay was conducted by using real-time PCR amplifier (Bio-Rad), an RT-qPCR kit, and corresponding primers. The upstream and downstream primers of the Actin and FcγRIII are as follows:

```
Actin-F:
                                  (SEQ ID NO: 1)
5'-GGAGGGGGTTGAGGTGTT-3'

Actin-R:
                                  (SEQ ID NO: 2)
5'-GTGTGCACTTTTATTGGTCTCAA-3'

FcγRIII-F:
                                  (SEQ ID NO: 3)
5'-AGACAGGCAGAGTGCAGC-3'

FcγRIII-R:
                                  (SEQ ID NO: 4)
5'-GTCCCTTCGCACATCAGTGT-3'
```

1.5 Western Blot

To investigate the expression of FcγRIII, the inventors further detected protein levels of FcγRIII in lung tissues of mice with silicosis. Separately, 20 mg each of the above cryopreserved lung tissues were weighed, supplemented with Protein Lysis Buffer, fully homogenized, and centrifuged at 4° C. and 12,000 rpm for 15 min to collect supernatants. The protein concentration was detected by using a BCA Protein Assay Kit. The protein supernatant was supplemented with loading buffer, denatured in a 95° C. metal bath pot, and stored at −80° C. in the long term. The above denatured protein was added to the loading well for protein gel electrophoresis. An electroporator and a nitrocellulose (NC) membrane were used for electrotransfer, and the NC membrane with protein was incubated with primary antibodies (anti-Actin, Invitrogen, the USA; and anti-FcγRIII, abcam, the UK) and secondary antibody successively. Finally, development was conducted by chemiluminescence instrument.

Figure 2A:
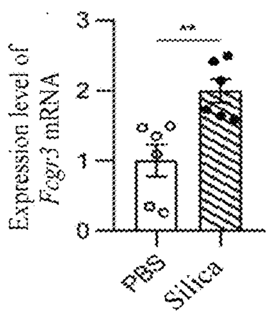
FIG. 2A-B illustrates relative mRNA levels and protein expression levels of FcγRIII in lung tissues of mice in the PBS group and the silica group, where
Figure 2B:
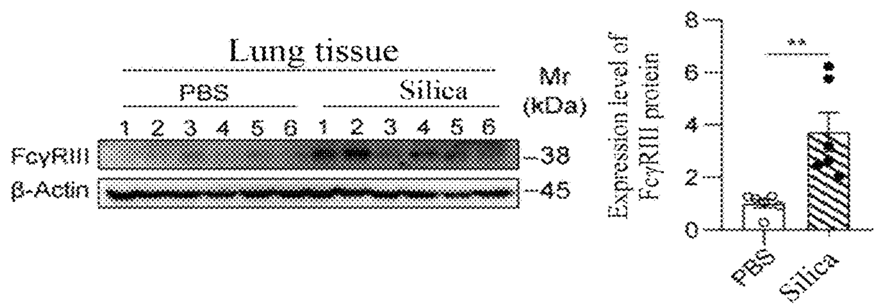

Results in FIG. 2A-B showed that mRNA and protein levels of FcγRIII were significantly upregulated in lung tissues of mice with silicosis. Therefore, FcγRIII can participate in the development and progression of silicosis.

Example 2

FcγRIII-Mediated Macrophage Phagocytosis of Silica 2.1 Establishment of an Fcgr3 knockdown stable MH-S cell line (1) Construction of an shRNA plasmid: Primers were designed using Vector NTI software and used for PCR amplification of a target gene. The target gene fragment was recovered by the gel extraction method, followed by digestion and ligation; the above DNA products were stored at −20° C. Subsequently, competent *Escherichia coli* was prepared, and the above DNA was added to a bacterial suspension for transformational culture Ampicillin was added to screen monoclonal strains, and identified by small-scale plasmid DNA extraction. Successfully constructed strains were further amplified and plasmid DNA was extracted therefrom. Subsequently, a virus was packaged with plasmid-transfected 293T cells, and a virus-containing supernatant was collected. The virus was used to treat MH-S cells, and the cells were screened by polybrene; a small amount of cells that finally survived were amplified, and their knockdown efficiency was identified; cells that were successfully knocked down were used for subsequent cell experiments. shRNA-3 1258-1278 primer sequence and knockdown functional sequences were as follows (synthesized by Invitrogen):

```
shRNA-F:
                                        (SEQ ID NO: 5)
5'-CCGGGCTAAGGGTTGATGGCATAGCCTCGAGGCTATGCCATCAACC
CTTAGCTTTTTG-3';

shRNA-R:
                                        (SEQ ID NO: 6)
5'-AATTCAAAAAGCTAAGGGTTGATGGCATAGCCTCGAGGCTATGCCA
TCAACCCTTAGC-3';
and

shRNA-3 1258-1278 functional sequence:
                                        (SEQ ID NO: 7)
GCTAAGGGTTGATGGCATAGC.
```

Figure 3:
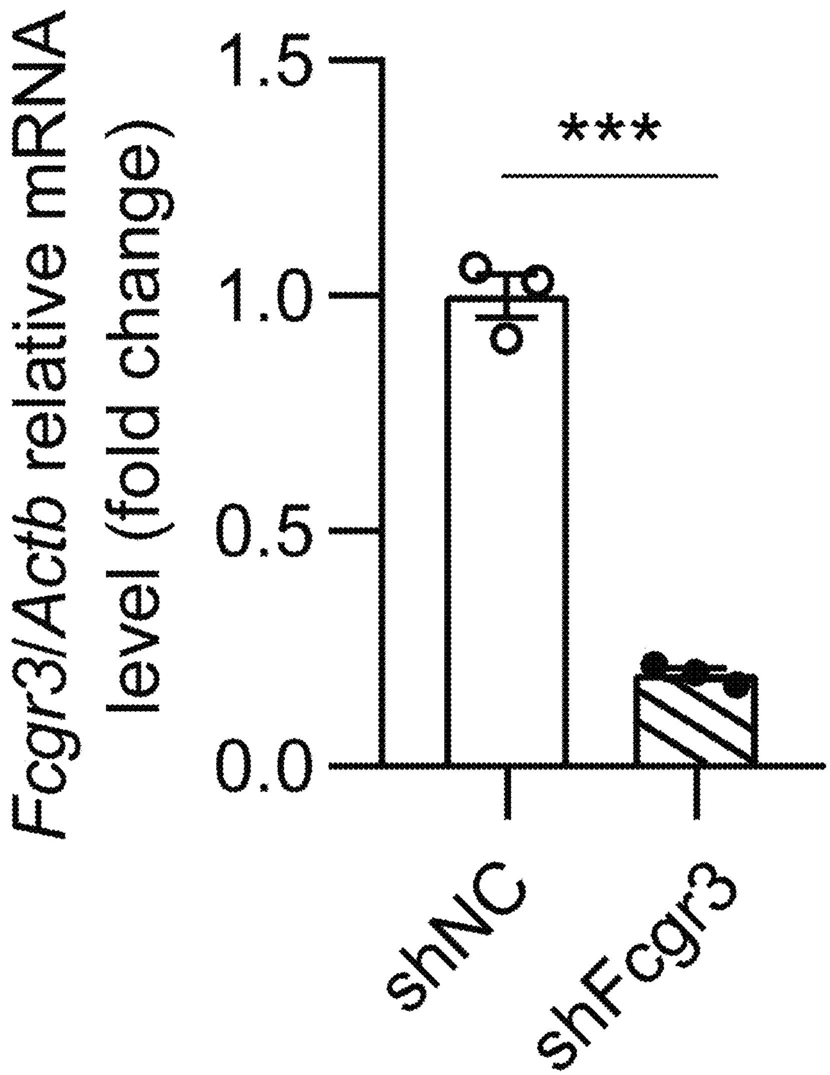
FIG. 3 illustrates a result of knockdown efficiency of shFcgr3.

From FIG. 3, the mRNA expression level of Fcgr3 was significantly downregulated, and an Fcgr3 knockdown stable MH-S cell line was established successfully.

2.2 Cell Stimulation with Silica shNC and shFcγRIII stable MH-S cell lines were seeded on a 35 mm Petri dish with a glass bottom, and each well contained $3\times10^5$ cells. After 12 h, 10 μM DID cell-labeling solution was added, and the cell lines were incubated in an incubator at 37° C. for 30 min and washed twice with the culture medium. Subsequently, 100 μg of silica was added to each well, and the cell lines were incubated in the incubator at 37° C. for 1 h and washed thrice with phosphate buffered saline (PBS). The supernatant was pipetted and discarded, the cell lines were fixed with 1 mL of 4% paraformaldehyde for 6 min; paraformaldehyde was pipetted and discarded, and 1 mL of $NH_4Cl$ was added to let the cell lines stand for 3 min. After washing with $ddH_2O$, 10 μL of mounting medium was added, photos were taken under a confocal microscope, and phagocytic index was calculated. Results are shown in FIG. 4.

Figure 4:
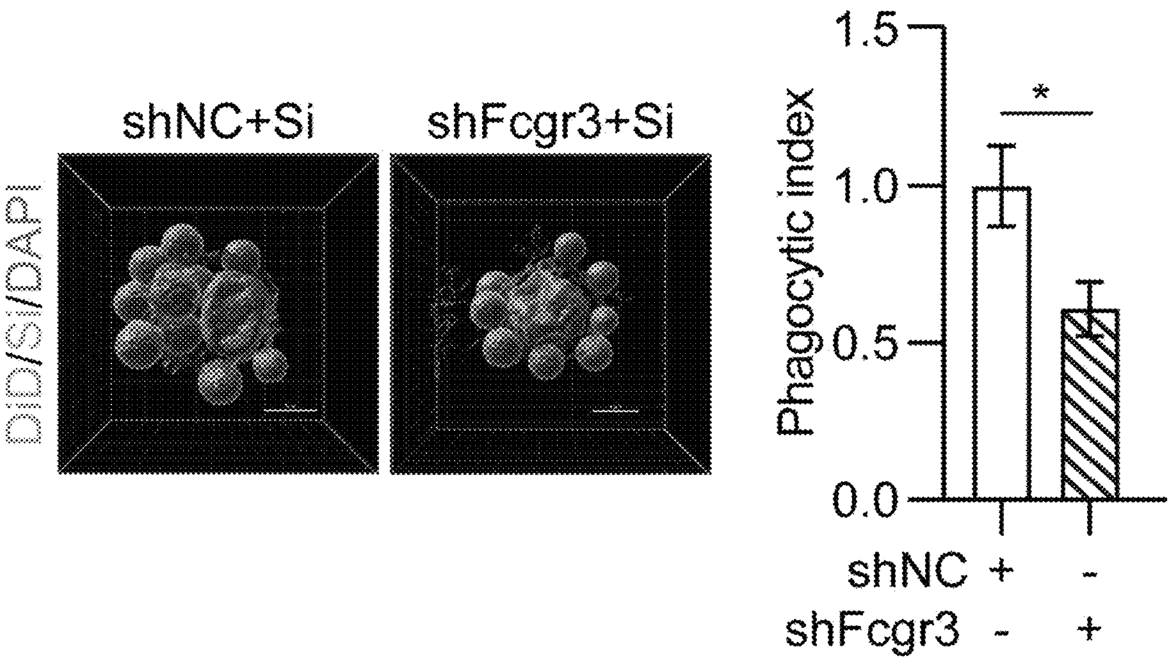
FIG. 4 illustrates a result of FcγRIII-mediated macrophage phagocytosis.

FIG. 4 shows that silica particles phagocytize in FcγRIII knockdown MH-S cells significantly decrease, indicating that FcγRIII participates in macrophage phagocytosis of silica.

Example 3

3.1 Establishment of a Silicosis Mouse Model

Male SPF-grade $Fc\gamma RIII^{+/+}$ mice and $Fc\gamma RIII^{-/-}$ mice (Jackson Laboratory) weighing 25-30 g and aged 8-10 weeks were selected. A silicosis mouse model was established by single-dose endotracheal instillation of 40 μL of silica suspension (200 mg/mL), and the control group was given control PBS at an equivalent dose. At six weeks after modeling, mouse pulmonary function was detected, and mouse lung tissues were collected to conduct inflammation and fibrosis evaluation, in order to determine the effect of FcγRIII deletion on silicosis phenotype. The grouping was as follows:

- WT+control group: Six $Fc\gamma RIII^{+/+}$ mice were subjected to endotracheal instillation of control PBS.
- KO+control group: Six $Fc\gamma RIII^{-/-}$ mice were subjected to endotracheal instillation of PBS.
- WT+silica group: Twelve $Fc\gamma RIII^{+/+}$ mice were subjected to endotracheal instillation of silica.
- KO+silica group: Twelve $Fc\gamma RIII^{-/-}$ mice were subjected to endotracheal instillation of silica.

3.2 Detection of Mouse Pulmonary Function

Spirometer was powered on and calibrated. A mouse was anesthetized with pentobarbital sodium, the cervical skin was incised to expose the trachea, an endotracheal tube was inserted, and the endotracheal tube was connected to the spirometer. Vital capacity (VC), lung compliance (Cdyn) and small airway resistance (R1) were detected.

3.3 HE Staining of Lung Tissues

A mouse left lung tissue was soaked in a 4% formalin solution for 48 h, dehydrated and embedded as a paraffin block. The paraffin block was stored in a −20° C. refrigerator. The lung tissue was sectioned to a thickness of 5 μm with a microtome, applied on a glass slide, and dried in a 60° C. oven. The sections were deparaffinized into water in xylene and gradient alcohol successively, dip-dyed in a hematoxylin staining solution for 11 min, rinsed with tap water, subjected to color separation with hydrochloric acid-alcohol, rinsed with tap water for 5 min, dip-dyed in an eosin staining solution for 9 min, and followed by conventional dehydration, permeabilization, and mounting; finally, the slides were photographed under a bright-field microscope, and photos were scored. The inflammation scoring criteria are shown in Table 1.

3.4 Masson Staining of Lung Tissues

The above lung tissue sections were preheated in the oven and deparaffinized into water according to the above method. The hematoxylin staining solution, fushsin staining solution, phosphomolybdic acid, and aniline blue were successively added dropwise on the sections for staining according to the instructions. Notably, color separation in hydrochloric acid-alcohol was needed and bluing was performed in tap water after hematoxylin staining; color separation in 1% acetic acid was needed after aniline blue staining. Subsequently, the sections were dehydrated in three vats of 100% ethanol successively, permeabilized in two vats of xylene, and finally mounted with neutral resin; the slides were photographed under a microscope and scored. The pulmonary fibrosis scoring criteria are shown in Table 2.

3.5 Hydroxyproline Detection

According to the instructions of the kit, 10 mg of mouse lung tissue was first weighed into an EP tube, supplemented with 100 μL of $ddH_2O$, fully homogenized, supplemented with 100 μL of 10 N NaOH, and baked in a 120° C. oven for 2 h. The sample was cooled, supplemented with 100 μL of 10 N HCl, and mixed well. The sample was centrifuged at 4° C. and 12,000 rpm for 5 min, and the supernatant was collected for detection. The standard was diluted according to the instructions, and subsequently the standard and the sample were added to a 96-well plate. The 96-well plate was placed in the oven to dry the moisture, and subsequently the corresponding detection reagent was added. Finally, a microplate reader was used to detect the absorbance value.

Figure 5:
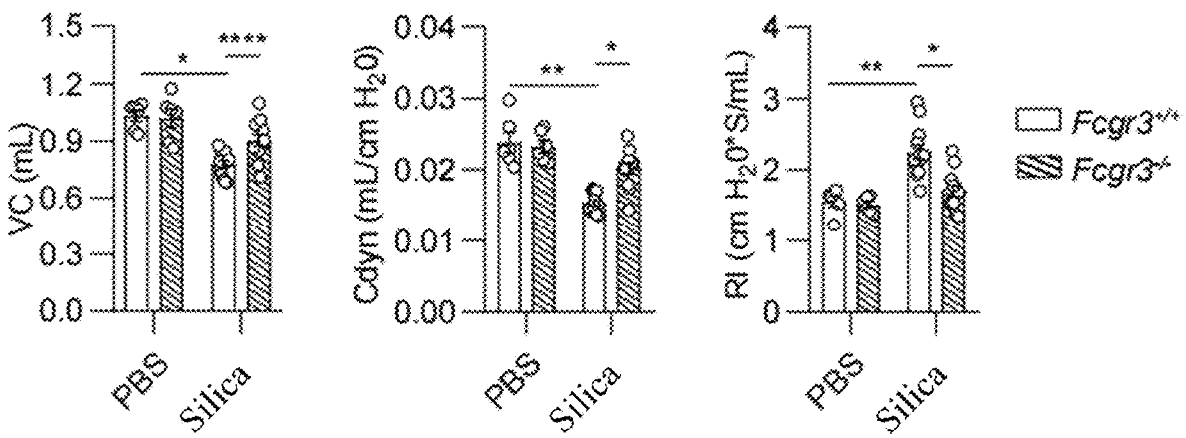
FIG. 5 illustrates effects of a whole-body Fcgr3 knockout on pulmonary function of mice with silicosis.
Figure 6:
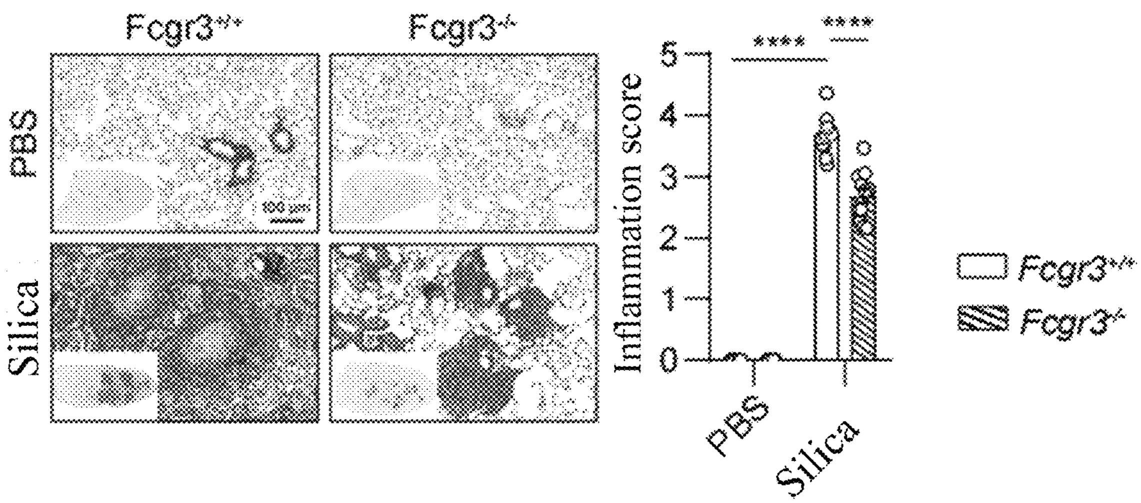
FIG. 6 illustrates effects of a whole-body Fcgr3 knockout on pulmonary inflammatory response of mice with silicosis.
Figure 7:
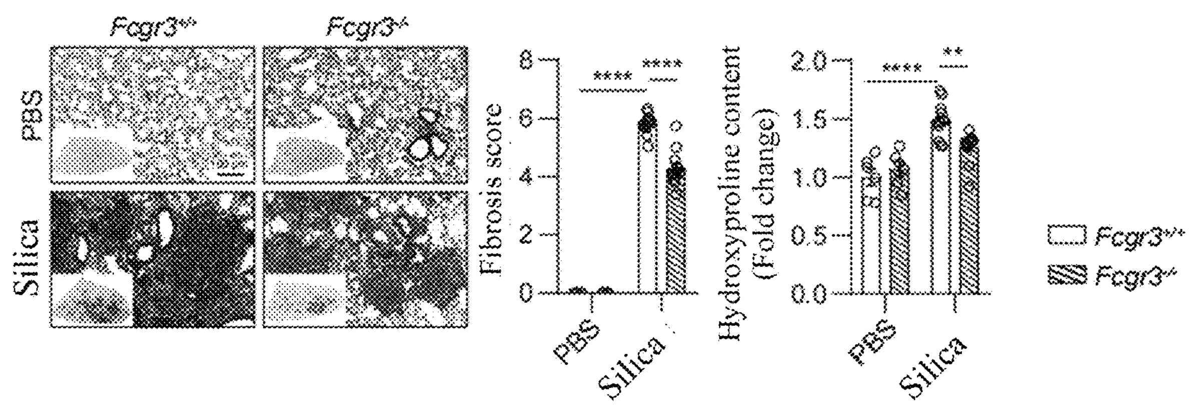
FIG. 7 illustrates effects of a whole-body Fcgr3 knockout on pulmonary fibrosis formation of mice with silicosis.

Results showed that $Fc\gamma RIII^{+/+}$ mice with exposure to silica showed apparent pulmonary dysfunction (FIG. 5); HE staining showed apparent nodules and inflammatory cell infiltration, and the inflammation score was significantly increased (FIG. 6); Masson staining showed more collagen fiber deposition in nodules, the fibrosis score was significantly increased, and the hydroxyproline content was significantly increased (FIG. 7); compared with the $Fc\gamma RIII^{+/+}$ mice, the pulmonary function, pulmonary inflammation, and fibrosis were significantly alleviated in $Fc\gamma RIII^{-/-}$ mice, indicating that complete knockdown of FcγRIII improved the pulmonary function of the mice with silicosis and alleviated the pulmonary inflammatory response and the formation of pulmonary fibrosis in the mice with silicosis (FIGS. 5 to 7).

Example 4

Establishment of a Silicosis Model and Intervention of Anti-FcγRIII Antibody 4.1 Establishment of a Silicosis Mouse Model Male SPF-grade C57BL/6J mice (Vital River) weighing 25-30 g and aged 8-10 weeks were selected. A silicosis mouse model was established by single-dose endotracheal instillation of μL of silica suspension (200 mg/mL), and the control group was given control PBS at an equivalent dose. Since Day 21 of modeling, the mice were subjected to endotracheal instillation of anti-FcγRIII antibody (Novus Biologicals, Germany) twice a week (2 μg/time), with a total of five injections; the control group was given IgG (Novus Biologicals, Germany; 2 μg/time). At six weeks after modeling, the mouse pulmonary function was detected, and mouse lung tissues were collected to conduct inflammation and fibrosis evaluation, in order to determine the effect of anti-FcγRIII antibody therapy on silicosis phenotype.

- Control+IgG group: Six mice were subjected to endotracheal instillation of control PBS; since Day 21 of modeling, they were subjected to endotracheal instillation of anti-IgG antibody weekly (2 μg/time), with a total of five injections.
- Control+anti-FcγRIII antibody group: Six mice were subjected to endotracheal instillation of PBS; since Day 21 of modeling, they were subjected to endotracheal instillation of anti-FcγRIII antibody weekly (2 μg/time), with a total of five injections.
- Silica+IgG group: Twelve mice were subjected to endotracheal instillation of silica; since Day 21 of modeling, they were subjected to endotracheal instillation of anti-IgG antibody weekly (2 μg/time), with a total of five injections.
- Silica+anti-FcγRIII antibody group: Twelve mice were subjected to endotracheal instillation of silica; since Day 21 of modeling, they were subjected to endotracheal instillation of anti-FcγRIII antibody weekly (2 μg/time), with a total of five injections.

4.2 Detection of Mouse Pulmonary Function

Spirometer was powered on and calibrated. A mouse was anesthetized with pentobarbital sodium, the cervical skin was incised to expose the trachea, an endotracheal tube was inserted, and the endotracheal tube was connected to the spirometer. Vital capacity, lung compliance and small airway resistance were detected.

4.3 Hydroxyproline Detection

According to the instructions of the kit, 10 mg of mouse lung tissue was first weighed into an EP tube, supplemented with 100 μL of $ddH_2O$, fully homogenized, supplemented with 100 μL of 10 N NaOH, and baked in a 120° C. oven for 2 h. The sample was cooled, supplemented with 100 μL of 10 N HCl, and mixed well. The sample was centrifuged at 4° C. and 12,000 rpm for 5 min, and the supernatant was collected for detection. The standard was diluted according to the instructions, and subsequently the standard and the sample were added to a 96-well plate. The 96-well plate was placed in the oven to dry the moisture, and subsequently the corresponding detection reagent was added. Finally, a microplate reader was used to detect the absorbance value.

Figure 8:
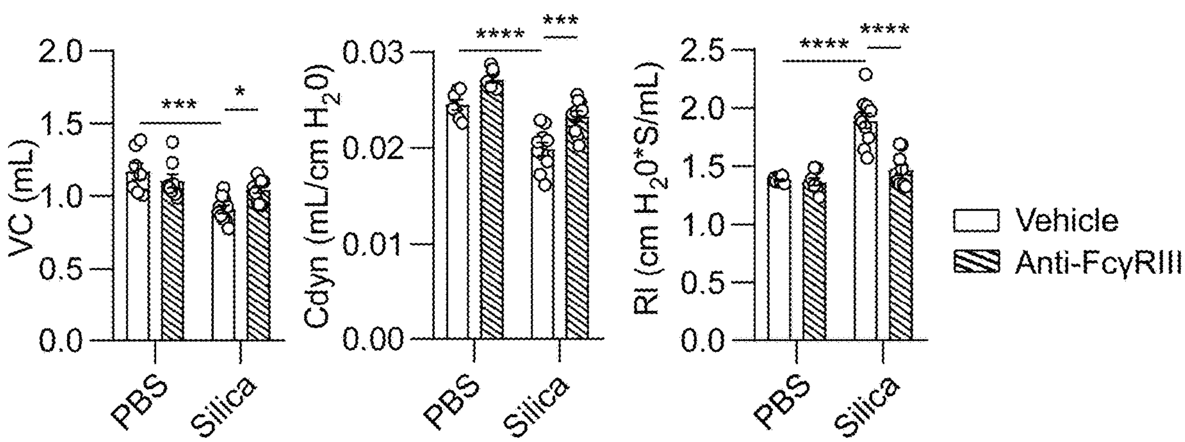
FIG. 8 illustrates effects of intratracheal administration of anti-FcγRIII antibody on pulmonary function of mice with silicosis.
Figure 9:
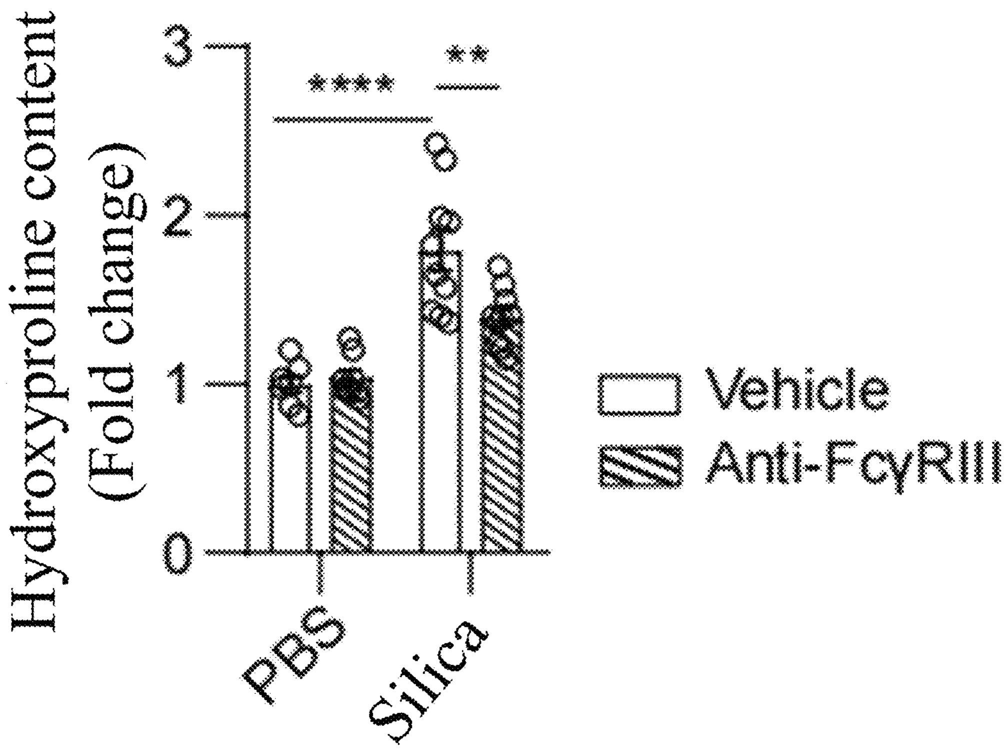
FIG. 9 illustrates effects of intratracheal administration of anti-FcγRIII antibody on pulmonary fibrosis formation of mice with silicosis.

Results showed that the mice with exposure to silica showed apparent pulmonary dysfunction; hydroxyproline monitoring showed increased collagen deposition in mouse lungs. The pulmonary function and fibrosis were significantly alleviated in mice treated with anti-FcγRIII antibody, indicating that administration of anti-FcγRIII antibody improved the pulmonary function of the mice with silicosis and alleviated the formation of pulmonary fibrosis in the mice with silicosis (FIGS. 8 to 9).

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A composition for treating pulmonary fibrosis, comprising an active ingredient and pharmaceutically acceptable carriers, wherein the active ingredient is an shRNA plasmid wherein a functional sequence for knockdown in the shRNA plasmid is SEQ ID NO: 7.

* * * * *